United States Patent
Eller et al.

(10) Patent No.: US 6,350,923 B1
(45) Date of Patent: Feb. 26, 2002

(54) HYDROGENATION OF ALDEHYDES

(75) Inventors: Karsten Eller, Ludwigshafen; Peter Wahl, Ladenburg; Rolf Pinkos, Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/472,798

(22) Filed: Dec. 28, 1999

(30) Foreign Application Priority Data

Dec. 28, 1998 (DE) .......................................... 198 60 489

(51) Int. Cl.⁷ .............................................. C07C 29/141
(52) U.S. Cl. ....................................... 568/853; 568/862
(58) Field of Search ................................. 568/853, 862

(56) References Cited

U.S. PATENT DOCUMENTS

| | | | | |
|---|---|---|---|---|
| 4,740,639 A | * | 4/1988 | Beavers ........................ | 568/853 |
| 5,304,685 A | * | 4/1994 | Merger et al. .............. | 568/433 |
| 5,364,984 A | * | 11/1994 | Arntz et al. ................. | 568/862 |
| 5,945,570 A | * | 8/1999 | Arhancet et al. ............ | 568/862 |

OTHER PUBLICATIONS

Ullmanns'Encyclopedia of Industrial Chemistry, 5th Edition, 1997, pp. 305–307.
Hodge et al., (Youji Huaxue 9(1989) 521; CA 112: 998/8p).
Shim et al.,(Tuaeha Hwahakhoe Chi 30 (1986) 101; CA 106; 66709).

* cited by examiner

Primary Examiner—Peter O'Sullivan
(74) Attorney, Agent, or Firm—Keil & Weinkauf

(57) ABSTRACT

A dialdehyde, trialdehyde or tetraldehyde or at least two thereof as aldehyde are hydrogenated by bringing into contact at least:
  the aldehyde;
  a catalyst comprising at least one metal selected from the group consisting of nickel, cobalt and copper in chemically bound and/or elemental form;
  hydrogen;
at a gas pressure in the range from 5 to 350 bar and a temperature in the range from 40 to 300° C.

14 Claims, No Drawings

HYDROGENATION OF ALDEHYDES

The invention relates to a process for hydrogenating a dialdehyde, trialdehyde or tetraaldehyde.

The catalytic hydrogenation of dialdehydes, trialdehydes or tetraaldehydes, preferably dialdehydes, in particular glutaraldehyde, for preparing corresponding alcohols, in particular dialcohols, especially 1,5-pentanediol, is a process which is of considerable commercial importance in the basic chemicals industry.

It can be seen from Ullmann's Encyclopaedia of Industrial Chemistry, 5th Edition, 1997, pp. 305–307, that, for example, 1,5-pentanediol is produced industrially by catalytic hydrogenation of glutaric acid or its esters. However, fewer processes for preparing 1,5-pentanediol from glutaraldehyde are known.

Thus, Hodge et al. (Youji Huaxue 9 (1989) 521; CA 112: 998/8p) discloses hydrogenation over an anion-exchange resin which has previously been loaded with borohydride ions. This is a stoichiometric reduction since the borohydride ions are consumed. This process is accordingly not usable for catalytic hydrogenation and is therefore not of industrial interest.

Shim et al., (Tuaeha Hwahakhoe Chi 30 (1986) 101; CA 106; 66709) discloses a homogeneously catalysed reduction of glutaraldehyde to pentanediol using carbon monoxide as reducing agent and catalytic amounts of $Rh_6(CO)_6$ or $Fe(CO)_5$. This process, too, is so costly that it is not of industrial interest.

It is an object of the present invention to provide a process and a catalyst which allows the catalytic hydrogenation of dialdehydes, trialdehydes or tetraaldehydes to give the corresponding alcohols in high yield under advantageous process conditions, e.g. temperature, pressure and operating life, and is thus inexpensive and industrially useful.

We have found that this object is achieved by a process for hydrogenating a dialdehyde, trialdehyde or tetraaldehyde or at least two thereof as aldehyde by bringing into contact at least the aldehyde, a catalyst comprising at least one metal selected from the group consisting of nickel, cobalt and copper in chemically bound and/or elemental form and hydrogen at a gas pressure in the range from 5 to 350 bar and a temperature in the range from 40 to 300° C. Among the abovementioned metals, nickel and copper are preferred and nickel is particularly preferred.

According to the present invention, it is preferred that the catalyst further comprises at least one metal selected from the group consisting of zirconium, copper, molybdenum, aluminum and manganese in chemically bound and/or elemental form. Furthermore, the presence of noble metals can have an advantageous effect on the catalyst. The noble metals are preferably used in smaller amounts than the abovementioned metals, in particular smaller amounts than nickel, cobalt or copper.

Another catalyst which is preferred according to the present invention is formed from noble metals as hydrogenation-active metals, which are preferably supported. In the case of catalysts comprising noble metals as hydrogenation-active metals, it is particularly preferred that other hydrogenation-active metals in particular nickel, cobalt or copper, are not present in such a catalyst.

For the purposes of the present invention, "chemically bound" means that the metal present in the catalyst is combined with at least one further, preferably nonmetallic, element to form a chemical compound. The nonmetallic elements are preferably elements of main groups V, VI and VII, with preference being given to those of main group VI, particularly preferably oxygen.

The constituents of the catalyst are present in elemental form when the metallic constituents are present in the oxidation state zero. In general, at least part of the metals used in the catalyst are present in elemental form, in particular during the reduction reaction to be catalysed.

The catalysts can be in the form of unsupported or supported catalysts.

The unsupported catalysts contain no further constituents, particularly constituents which function as a support, in addition to the constituents required for the catalytic reaction.

The amount of hydrogenation-active metal, calculated as metal oxide regardless of the form in which it is actually present, is preferably in the range from 80 to 100% by weight, based on the metal oxide, in the case of unsupported catalysts. The remainder can be made up by promoters. The function of the promoter is, in particular, to increase activity and selectivity in the hydrogenation. Particularly preferred promoters are, for example, molybdenum or manganese, preferably in the form of their oxides.

In the case of supported catalysts, the amount of the hydrogenation-active metal(s) or oxide(s) is lower because of the use of the support. Preference is given to using from 30 to 70% by weight of metal oxide(s), regardless of the actual hydrogenation-active form, based on the supported catalyst.

Supported catalysts comprise not only those constituents which are predominantly responsible for the catalytic reaction but also further constituents which do not participate directly in the catalytic reaction and are first and foremost responsible for the mechanical stability of the catalyst. One group of support materials consists of oxidic supports. Oxidic supports which have been found to be usefull are, in particular, zirconium dioxide, titanium oxide, aluminum oxide and silicon oxides. Among these, zirconium dioxide is particularly preferred as support.

Another group of support materials consists of activated carbon and graphite. These supports have been found to be particularly useful when the starting material to be hydrogenated is used as a suspension.

A further group of supports consists of solid bodies of inert materials, for example metal, plastic or ceramic, for example SiC, $Si_3N_4$ or $W_2N$, preferably metal.

The supports used can have any shape, but preference is given to powders, extrudates, pellets, spheres or rings. The production of the supports can be carried out by the usual generally known methods, as can the application of the metal or noble metal components. In this context, the following information may be provided.

In general, the unsupported catalysts used according to the present invention are obtained from the aqueous solutions of the water-soluble salts of their constituents by precipitation, drying, shaping, if desired calcination and subsequent firing, generally in the presence of oxygen, in a temperature range from 200 to 1000° C.

In the case of the supported catalysts, the above-described process for producing the unsupported catalysts is supplemented by the following, methods of applying the constituents to the support:

In particular, the following application methods are useful:

a) Application of a constituent salt solution to a previously produced inorganic support in one or more impregnation steps. Subsequent to impregnation, the support is dried and, if desired, calcined.

a1) Impregnation can be carried out by the "incipient wetness" method in which the support is treated with an amount of impregnation solution which is not more than that corresponding to the water absorption capacity of the support. However, impregnation can also be carried out with excess solution.

a2) In multistage impregnation methods, it is advantageous to dry and possibly calcine the impregnated support between individual impregnation steps. Multistage impregnation is particularly advantageous when the support is to be treated with a relatively large amount of constituent or is to be impregnated with a plurality of components.

a3) In the impregnation, the inorganic support material is preferably used in preshaped form, for example as powder, spheres, extrudates or pellets. Particular preference is given to using it as powder.

a4) As solvent for the constituent salts, use is made, for example, of concentrated aqueous ammonia.

b) Precipitation of a constituent salt solution onto a previously produced, inert inorganic support. In a particularly preferred embodiment, this is present as powder in an aqueous suspension.

b1) In one embodiment (i), a constituent salt solution is precipitated, preferably using sodium carbonate solution. As substrate, use is made of an aqueous suspension of the support material.

b2) In a further embodiment (ii), the precipitated catalyst can be produced in a two-stage process. In the first stage, a powder is produced as described in a) and dried. This powder is converted into an aqueous suspension and used as substrate in a procedure equivalent to that described in embodiment (i).

Precipitates resulting from a) or b) are filtered and preferably washed free of alkali in a customary fashion. Both the end products from a) and those from b) are dried at from 50 to 200° C., preferably at 150° C., and subsequently, if appropriate, dried at generally from 200 to 400° C., in particular from 210 to 260° C., preferably for 2 hours.

Suitable constituent salts are, in particular, bisulfates, nitrates, chlorides, carbonates, acetates, oxalates, molybdates or ammine complexes. For the metals cobalt, zirconium, copper and nickel, their nitrates have been found to be particularly useful for producing the catalyst. In the case of molybdenum, molybdate salts have been found to be particularly advantageous for producing the catalyst.

The calcination employed during the production of the catalyst is carried out at from 300 to 600° C., in particular from 400 to 500° C., for at least one hour, preferably from 2 to 5 hours and particularly preferably from 3 to 4 hours.

If the catalyst is to be used at least partially in its reduced form, it is reduced by bringing it into contact with hydrogen prior to the actual catalysis reaction. The prereduction of the catalyst can be carried out using pure hydrogen, but is preferably carried out using a hydrogen/inert gas mixture, particularly preferably a hydrogen/nitrogen mixture, at from 80 to 300° C., preferably from 150 to 250° C. and particularly preferably from 180 to 240° C. If a hydrogen/inert gas mixture is used, a proportion of hydrogen of from 1 to 80% by volume, preferably from 2 to 60% by volume is advantageous. A hydrogen/inert gas mixture can also be used in the catalysis reaction. In the reduction, it has been found to be particularly useful for the proportion of hydrogen in the inert gas mixture to be from 1 to 5% by volume in the first phase of the reduction and to be subsequently increased to from 5 to 20% by volume and finally to from 20 to 50% by volume. The amount of hydrogen or the hydrogen content of the inert gas mixture is particularly useful for controlling the reaction conditions, in particular the temperature, of the reduction. Thus, for example, a reduction in the amount of hydrogen or the hydrogen content can slow the temperature rise or lower the temperature.

In an advantageous embodiment of the catalyst production process, the water-soluble zirconium salt is partly, e.g. up to a proportion of 50% by weight, based on the zirconium used, or preferably completely replaced by solid zirconium dioxide or zirconium hydroxide or zirconium oxide hydroxide which is added to the aqueous metal salt solution prior to precipitation or is initially placed in the reaction vessel.

The catalyst is produced, for example, by mixing the aqueous solution of the metal salts simultaneously while stirring with an aqueous alkali metal carbonate solution, preferably sodium carbonate solution, as a result of which the metals precipitate in the form of a mixture of metal hydroxides and metal carbonates. The metal salt content of the metal salt solution is advantageously from 5 to 40% by weight. The aqueous alkali metal carbonate solution generally has a concentration of from 10 to 30% by weight, preferably from 15 to 25% by weight. The precipitation is carried out at from 30 to 90° C., preferably from 50 to 90° C., and a pH of from 5 to 9, preferably from 6 to 8.

The suspension obtained is filtered and washed with water until anions can no longer be detected. The solid is then, if desired, dried at from 120 to 200° C. in a drying oven or a spray drier. If molybdenum is desired as a catalyst constituent, it is preferably added as ammonium heptamolybdate to the moist filter cake. The dried filter cake is heated at from 400 to 600° C.

In a further embodiment of the present invention, it is preferred that the proportion of nickel used in the catalyst is greater than that of zirconium which is in turn greater than that of copper which is in turn grater than that of molybdenum, each in percent by weight based on NiO, $ZrO_2$, CuO and $MoO_3$ in the unhydrogenated catalyst.

In the catalysts used according to the present invention, nickel is preferably present in an amount of from 30 to 70% by weight, preferably from 40 to 60% by weight and particularly preferably from 45 to 55% by weight, based on NiO in the unhydrogenated catalyst. Zirconium is advantageously present in embodiments of the catalyst in amounts of from 15 to 45% by weight, preferably from 20 to 40% by weight and particularly preferably from 25 to 35% by weight, based on $ZrO_2$ in the unreduced catalyst. The amount of copper in embodiments of the catalyst to be used in the process of the present invention is preferably from 5 to 30% by weight, more preferably from 10 to 25% by weight and particularly preferably from 15 to 20% by weight, based on CuO in the unreduced catalyst. Furthermore, it is advantageous for from 0.1 to 10% by weight, preferably from 0.5 to 5% by weight and particularly preferably from 1 to 3% by weight, of molybdenum to be present in the catalyst, based on $MoO_3$ in the unreduced catalyst.

In a further embodiment of the catalyst used according to the present invention, it is possible for the catalyst to contain, in place of or in addition to molybdenum, cobalt in an amount of from 0.1 to 20% by weight, preferably from 1 to 5% by weight and particularly preferably from 1.5 to 3% by weight, based on CoO in the unreduced catalyst, and/or manganese in an amount of from 0.1 to 10% by weight, preferably from 1 to 5% by weight and particularly preferably from 1.5 to 3% by weight, based on MnO in the unreduced catalyst, and/or aluminum in an amount of from 0.1 to 10% by weight, preferably from 1 to 5% by weight and particularly preferably from 1.5 to 3% by weight, based on $Al_2O_3$ in the unreduced catalyst.

The percentages of constituents given for embodiments of the catalyst together with, if used, further generally known auxiliaries and additives add up to 100% by weight, based on the unreduced catalyst.

In a further embodiment, the catalyst used in the process of the present invention has the following composition in its oxidic, unreduced form: from 30 to 70% by weight, preferably from 40 to 60% by weight, in particular from 35 to 55% by weight, of nickel oxide, from 10 to 60% by weight, preferably from 15 to 50% by weight, in particular from 25 to 45% by weight, of zirconium dioxide, from 5 to 40% by weight, preferably from 10 to 35% by weight, in particular from 10 to 20% by weight, of copper oxide. The catalyst may further comprise from 0.1 to 5% by weight of molybdenum oxide and, if desired, for example from 0 to 10% by weight of manganese oxide.

In a different embodiment of the catalyst used according to the present invention, the proportion of zirconium is from 25 to 35% by weight, preferably from 28 to 33% by weight and particularly preferably from 29 to 32% by weight, based on $ZrO_2$ in the unreduced catalyst, the proportion of copper is from 12 to 22% by weight, preferably from 15 to 19% by weight and particularly preferably from 16 to 18% by weight, based on CuO in the unreduced catalyst, and the proportion of molybdenum is from 0.1 to 5% by weight, preferably from 1 to 4% by weight and particularly preferably from 1.5 to 2.5% by weight, based on $MoO_3$ in the unreduced catalyst. The abovementioned percentages by weight are made up to 100% by weight by the proportion of nickel, based on NiO in the unreduced catalyst.

In the process of the present invention, the catalyst can be used in a fixed bed for the hydrogenation. It is also possible to use the catalyst in a fluidized-bed reaction in the process of the present invention.

The process of the present invention can also be carried out by the trickle-bed method. In the trickle-bed method, the starting materials, namely a dialdehyde, trialdehyde or tetraaldehyde, preferably a dialdehyde, in the liquid phase are applied from above, preferably in finely divided form, to the catalyst bed in the reactor which is under hydrogen pressure, so that a thin film of the liquid phase is formed on the catalyst.

A further process variant which is preferred according to the present invention is the upflow procedure. Here, hydrogen gas is introduced into the reactor flooded with the liquid phase comprising the starting material, with the hydrogen rising as gas bubbles through the catalyst bed and the starting material being fed in from below.

The above-described process variants can be carried out either continuously or batchwise, preferably continuously. When the process of the present invention is carried out batchwise, the preferred procedure involves placing a dialdehyde, trialdehyde or tetraaldehyde, preferably a dialdehyde, if desired a further liquid, and the catalyst in a pressure autoclave, subsequently injecting hydrogen and then heating the autoclave to the reaction temperature. After the reaction is complete, the autoclave is vented and the reaction product is worked up, preferably by distillation, in order to obtain the corresponding alcohol.

Carrying out the reduction batchwise is particularly preferred in a reduction using a suspension catalyst. However, preference is generally given to carrying out the reduction process of the present invention continuously.

If the reaction is carried out continuously, preferably in a fixed-bed reactor, the LHSV over the catalyst is usually in a range from 0.05 to 2, preferably from 0.1 to 0.8 and particularly preferably from 0.2 to 0.7, $1_{aldehyde}1_{catalyst}^{-1}h^{-1}$, where the abovementioned LHSV figures are based on the pure aldehyde, in particular dialdehyde.

In general, the process of the present invention is carried out at a gas pressure in the range from 5 to 500 bar, preferably from 100 to 400 bar and particularly preferably from 150 to 250 bar, and at a temperature in the range from 40 to 400° C., preferably from 90 to 200° C. and particularly preferably from 100 to 180° C.

The dialdehydes, trialdehydes or tetraaldehydes have up to 50, preferably up to 30 and particularly preferably up to 20, carbon atoms. Particular preference is given to dialdehydes, trialdehydes or tetraaldehydes which have from 1 to 20, preferably from 2 to 10 and particularly preferably from 3 to 6, carbon atoms. Among the abovementioned aldehydes, particular preference is given to dialdehydes.

In the process of the invention, preference is given to using dialdehydes having from 2 to 50, preferably from 3 to 20 and particularly preferably from 4 to 10, carbon atoms. In the case of dialdehydes having 3 or more carbon atoms, it is preferred that the carbon atoms forming the aldehyde groups are located at the end of the corresponding carbon chain. The process of the present invention is preferably used for reducing glutaraldehyde to 1,5-pentanediol, glyoxal to ethylene glycol, 1,4-butanedialdehyde to 1,4-butanediol and 1,6-hexanedialdehyde to 1,6-hexanediol, particularly preferably for reducing glutaraldehyde to 1,5-pentanediol.

In the process of the present invention, it is preferred that the aldehyde is used as liquid phase with at least one phase former. The liquid phase can be either heterogeneous or homogeneous. In the case of a homogeneous liquid phase, the aldehyde is preferably present as a solution in at least one phase former. Suitable phase formers are compounds which are liquid at ambient temperature. The phase formers can be either organic or inorganic compounds. Phase formers which have been found to be useful are, in particular, $C_1$–$C_{10}$-alcohols, tetrahydrofuran, N-methylpyrrolidone, dimethylacetamide, dimethylformamide and water. However, particular preference is given to water and the abovementioned alcohols, especially water. The aldehyde is preferably present in the liquid phases in amounts of from 5 to 80% by weight, preferably from 20 to 70% by weight and particularly preferably from 40 to 60% by weight, based on the total liquid phase.

According to the present invention, preference is given to using an above-described catalyst for reducing a dialdehyde, in particular glutaraldehyde, to a diol, in particular 1,5-pentanediol.

Furthermore, a diol, in particular 1,5-pentanediol, obtainable by the process of the present invention is also preferred according to the present invention.

The present invention is illustrated by the non-limiting examples below.

EXAMPLES

Example 1

500 ml of a catalyst which comprised about 50% by weight of NiO, 17% by weight of CuO, 31% by weight of $ZrO_2$ and 2% by weight of $MoO_3$ and had been diluted with 400 ml of V2A rings were installed in an electrically heated tube reactor. The catalyst was not reduced. At 120° C. and 200 bar of hydrogen pressure, 100 ml/h of a 50% strength aqueous glutaraldehyde solution was passed over the catalyst in the upflow mode. At complete conversion, a selectivity to 1,5-pentanediol of 98% was found.

Example 2

Example 2 was carried out using a method analogous to Example 1, but 200 ml/h of glutaraldehyde solution were passed over the catalyst. The yield remained unchanged and the selectivity was likewise 98%.

Example 3

Example 3 was carried out using a method analogous to Example 1, but 300 ml/h of glutaraldehyde solution were passed over the catalyst. The yield remained unchanged and the selectivity was likewise 98%.

Example 4

Example 4 was carried out using a method analogous to Example 1, but 600 ml/h of glutaraldehyde solution were passed over the catalyst. The yield remained unchanged and the selectivity was likewise 98%.

Example 5

The reaction product from Example 4 was distilled batchwise using a column having 33 theoretical plates. After taking off the water, pentanediol having a purity of 99.2% was isolated at 45 mbar, 158° C. at the top and 210° C. at the bottom and a reflux ratio of 5:1. The distillation yield was about 90%.

We claim:

1. A process for hydrogenating at least one dialdehyde, trialdehyde or tetraldehyde to the corresponding alcohol(s), said process comprising the step of contacting at least: the dialdehyde(s), trialdehyde(s) and/or tetraldehyde(s) a catalyst comprising at least one metal selected from the group consisting of nickel, cobalt and copper and further at least two other metals selected from zirconium, molybdenum, aluminum and manganese, the metals being in chemically bound and/or elemental form; and hydrogen at a gas pressure in the range of from 5 to 350 bar and at a temperature in the range from 40 to 300° C.

2. The process as claimed in claim 1, wherein the catalyst in addition to nickel, cobalt and/or copper, further comprises two or more of the constituents selected from zirconium, molybdenum, aluminum and manganese in chemically bound or elemental form.

3. The process as claimed in claim 1, wherein the aldehyde is used as a liquid phase with at least one phase former.

4. The process as claimed in claim 3, wherein the phase former is water.

5. The process as claimed in claim 1, wherein the catalyst is supported.

6. The process as claimed in claim 2, wherein the catalyst comprises nickel in a proportion greater than that of zirconium which is greater than that of copper which is greater than that of molybdenum, each in % by weight based on the respective metal oxides in the unhydrogenated catalyst.

7. The process as claimed in claim 1, wherein a dialdehyde is reduced to a diol.

8. The process as claimed in claim 7, wherein glutaraldehyde is reduced to 1,5-pentanediol.

9. The process as claimed in claim 5, wherein a dialdehyde is reduced to a diol.

10. The process as claimed in claim 9, wherein glutaraldehyde is reduced to 1,5-pentanediol.

11. A process as claimed in claim 1, wherein a catalyst is used which comprises at least one metal selected from the group consisting of nickel, cobalt and copper, and further at least one other metal, the metals being in chemically bound and/or elemental form, for reducing a dialdehyde to a diol.

12. The process as claimed in claim 11, wherein the catalyst is used for reducing glutaraldehyde to 1,5-pentanediol.

13. The process as claimed in claim 11, wherein the catalyst is a supported catalyst.

14. The process as claimed in claim 12, wherein the catalyst is a supported catalyst.

* * * * *

UNITED STATES PATENT AND TRADEMARK OFFICE
CERTIFICATE OF CORRECTION

PATENT NO. : 6,350,923 B1
DATED : February 26, 2002
INVENTOR(S) : Eller et al.

It is certified that error appears in the above-identified patent and that said Letters Patent is hereby corrected as shown below:

<u>Column 7,</u>
Line 31, "two other metals" should be -- one other metal --.

Signed and Sealed this

Thirteenth Day of August, 2002

Attest:

Attesting Officer

JAMES E. ROGAN
*Director of the United States Patent and Trademark Office*